United States Patent [19]

Burnier et al.

[11] Patent Number: 5,736,574

[45] Date of Patent: Apr. 7, 1998

[54] PHARMACCEUTICAL/COSMETIC COMPOSITIONS COMPRISING SYNERGISTIC ANTIMICROBIAL ADMIXTURE

[75] Inventors: Véronique Burnier, Chatellerault; Jean Pierre Brissonnet, Poitiers, both of France

[73] Assignee: La Roche Posay Laboratoire Pharmaceutique, La Roche Posay, France

[21] Appl. No.: 649,192

[22] Filed: May 17, 1996

[30] Foreign Application Priority Data

May 17, 1995 [FR] France .................... 95 05866

[51] Int. Cl.⁶ ................. A61K 31/195; A61K 31/08
[52] U.S. Cl. ............................ 514/568; 514/723
[58] Field of Search .................. 514/563, 723

[56] References Cited

FOREIGN PATENT DOCUMENTS 2411006  7/1979  France .
2415750  10/1974  Germany .
4140474  6/1993  Germany .
4240674  3/1994  Germany .

OTHER PUBLICATIONS

CA 82:119599, Astruc et al., 1974.
Ann. Pharm. Fr., vol. 39, No. 6, 1981, pp. 503–510.
Antimicrob. Agents Chemother., 1994, 38/7 (1523–1529).
Lipids, 1990, vol. 25, No. 2, pp. 119–121.
J. Biol. Chem., 1986, vol. 261, No. 14,, pp. 6338–6344.
Proc. Soc. Exp. Biol. Med., 1991, vol. 197, No. 1, pp. 91–97.

Primary Examiner—Kimberly Jordan
Attorney, Agent, or Firm—Burns, Doane, Swecker & Mathis, L.L.P.

[57] ABSTRACT

Combinatory antimicrobial immixtures comprising at least one antimicrobial hydrolipid and/or lipid and an antimicrobially synergistically effective amount of at least one glyceryl monoalkyl ether are well suited for formulation, as preservatives, into a wide variety of pharmaceutical/cosmetic compositions.

21 Claims, No Drawings

PHARMACCEUTICAL/COSMETIC COMPOSITIONS COMPRISING SYNERGISTIC ANTIMICROBIAL ADMIXTURE

BACKGROUND OF THE INVENTION

1. Technical Field of the Invention

The present invention relates to pharmaceutical/cosmetic compositions comprising synergistic combination of at least one hydrolipid/lipid compound exhibiting antimicrobial activity and of at least one glyceryl monoalkyl ether synergist therefor.

2. Description of the Prior Art

It is common to introduce into cosmetic or dermatological compositions chemical preservatives intended to combat the growth of microorganisms therein, which would rapidly render such compositions unsuitable for use. These compositions have to be protected both against microorganisms likely to grow within same and against those which the user may introduce thereto via handling, and in particular when products in a jar are manipulated by the fingers.

Typical chemical preservatives include, in particular, parabens or formaldehyde donors. These preservatives present the drawback of causing intolerance, such as irritations and/or allergies, and in particular on sensitive skins. This is likewise the case for alcohols or polyols, such as ethanol or propylene glycol, in particular when they are present at relatively high concentrations.

Thus, need continues to exist for antimicrobial agents having an activity which is at least as effective as the compounds of the prior art, but which do not present the drawbacks associated therewith.

It is also known to this art that lipoamino acids or lipids exhibit a certain antimicrobial activity. However, this activity may sometimes prove to be insufficient. If they are present at relatively high levels, these lipoamino acids or lipids may also elicit an intolerance response, more particularly when they comprise short-chain fatty acids.

SUMMARY OF THE INVENTION

It has now surprisingly been determined that combinatory immixture of at least one compound exhibiting antimicrobial activity, selected from among the hydrolipids or lipids, and at least one glyceryl monoalkyl ether, manifests a synergistic effect with regard to the antimicrobial activity of the combination.

The antimicrobial action of this combination is advantageous since it is milder, while at the same time being at least as effective as that of the compounds of the prior art, insofar as no intolerance is experienced and no redness is observed when a cosmetic or dermatological composition comprising this combinatory immixture is topically applied to the skin.

Thus, the present invention features combinatory immixture of at least one compound exhibiting antimicrobial activity, selected from among the hydrolipids or lipids, and at least one glyceryl monoalkyl ether.

This invention also features pharmaceutical/cosmetic compositions comprising the aforesaid admixture.

The present invention also features antimicrobial agents comprising the aforesaid combinatory immixtures.

DETAILED DESCRIPTION OF BEST MODE AND SPECIFIC/PREFERRED EMBODIMENTS OF THE INVENTION

More particularly according to the present invention, the subject combinatory immixtures are well suited for cosmetic or pharmaceutical use, preferably dermatological use. More especially, the cosmetic or pharmaceutical composition according to the invention are applied topically.

In the context of pharmaceutical applications, the present invention features the aforesaid combination as an antimicrobial agent for the formulation of pharmaceutical compositions, more particularly dermatological compositions.

According to the invention, by the expression "antimicrobial activity" is intended an antibacterial activity and/or an antifungal activity and/or an antiviral activity.

Also according to the invention, by the term "hydrolipid" are intended products resulting from the coupling of fatty acids with hydrophilic molecules selected from among amino acids (monomers, peptides or proteins) and polysaccharides. This coupling of the two compounds may produce compounds containing covalent bonds, in particular between the amino acids and the fatty acids (of the —CONH— type), but also compounds containing non-covalent bonds. Preferably, hydrolipids having only covalent bonds are employed.

The fatty acids present in the hydrolipids are branched or unbranched and saturated or unsaturated. They generally have from 6 to 18 and preferably from 6 to 12 carbon atoms.

When the hydrolipids comprise amino acids, these are thus in the form of monomers, peptides or proteins. The monomer form is the preferred.

Exemplary such amino acids include methionine, lysine, aspartic acid, glycine and cysteine. The amino acids are preferably glycine or cysteine. N-n-Octanoylglycine, marketed by Seppic under the trademark Lipacid® C8G, is particularly preferred.

The proteins may be of natural or synthetic origin. They may be present in hydrolyzed form, in which case they are peptides or amino acids.

Thus, among the proteins of animal origin which are preferred are keratin, silk, collagen, reticulin, elastin, lactalbumin, lactoglobulin, casein and ovalbumin. Among the proteins of plant origin which are preferred are proteins from wheat, from corn, from oats, from soya and from almond. Among the proteins of marine origin which are preferred are collagen and proteins from fish, from molluscs, from crustaceans and from algae.

Certain of these hydrolipids, more commonly referred to as lipoamino acids, resulting from the reaction between fatty acids, as described above, and amino acids, as described above, are set forth in particular in FR-2,192,795, FR-2,411,006 and FR-2,422,400.

When the hydrolipids comprise polysaccharides, these may be of natural or synthetic origin.

Thus, among the polysaccharides of animal origin which are exemplary, in particular, are hyaluronic acid, chondroitin 4-sulfate, chondroitin 6-sulfate, dermatan sulfate, heparan sulfate, keratan sulfate and heparin and derivatives thereof.

Among the polysaccharides of plant origin which are exemplary are amylose, amylopectin, glucomannans, galactomannans, fructosans, cellulose gums and derivatives thereof.

Among the polysaccharides of marine origin which are exemplary are chondroitin sulfate, chitosan, alginates, agar and carrageenan.

When these polysaccharides are of synthetic origin, they may be obtained by fermentation. Exemplary thereof are xanthan, gellan, curdlan and dextran.

Commercially available hydrolipids which are also exemplary are the products of the "Lifidrem®" family marketed by Coletica, such as Lifidrem® Coun (hydrophilic molecule: collagen, fatty acid: undecylenic acid), Blun (hydrophilic molecule: wheat proteins, fatty acid: undecylenic acid), Avun (hydrophilic molecule: oat proteins, fatty acid: undecylenic acid), Amun (hydrophilic molecule: sweet almond proteins, fatty acid: undecylenic acid), Syun (hydrophilic molecule: soya proteins, fatty acid: undecylenic acid), Arun (hydrophilic molecule: pink alga proteins, fatty acid: undecylenic acid), Arca (hydrophilic molecule: pink alga proteins, fatty acid: caprylic acid).

According to the invention, by the term lipid are intended branched or unbranched, saturated or unsaturated fatty acids. They generally have from 6 to 18 and preferably from 6 to 12 carbon atoms. Exemplary thereof are caprylic acid, capric acid, lauric acid, myristic acid, myristoleic acid, palmitic acid, palmitoleic acid, oleic acid, linoleic acid, linolenic acid and undecylenic acid. Among these, caprylic acid, capric acid, lauric acid and undecylenic acid are the preferred.

Hydrolipids and more particularly lipoamino acids are preferably used according to the invention.

The glyceryl monoalkyl ethers used characteristically have the following formula (I):

R—O—CH$_2$—CHOH—CH$_2$OH    (I)

in which R is a linear or branched, saturated or unsaturated alkyl radical having from 3 to 14 carbon atoms, in particular 5 to 12 carbon atoms, preferably 7 to 12 carbon atoms.

Among these compounds, particularly exemplary are 1-heptyl glyceryl ether, 1-(2-ethylhexyl) glyceryl ether, 1-octyl glyceryl ether, 1-decyl glyceryl ether and 1-dodecyl glyceryl ether. Among these, 1-(2-ethylhexyl) glyceryl ether is preferred.

The weight ratio of the compound exhibiting antimicrobial activity to the glyceryl monoalkyl ether may vary over a wide range. It preferably ranges from 0.05 to 30 and more particularly from 0.1 to 5.

The combinatory immixtures according to the invention are more particularly intended for cosmetic or pharmaceutical use, preferably for dermatological use.

In particular, this cosmetic or pharmaceutical composition according to the invention is applied topically.

This synergic combination thus presents the advantage that the compound having antimicrobial activity may be present in lesser amounts in a composition than when it is used alone.

The composition preferably comprises from 0.01% to 6%, advantageously from 0.2% to 3%, by weight of glyceryl monoalkyl ether relative to the total weight of the composition.

The composition preferably comprises from 0.01% to 5%, advantageously from 0.2% to 3%, by weight of the compound exhibiting antimicrobial activity relative to the total weight of the composition.

The compositions of the invention, in particular for cosmetic or dermatological applications, may also comprise the cosmetic or pharmaceutical additives and adjuvants conventionally employed, such as fats or fatty substances, organic solvents, ionic or nonionic thickeners, softeners, antioxidants, opacifiers, stabilizers, silicones, anti-foaming agents, moisturizing agents, vitamins, fragrances, ionic or nonionic surfactants, fillers, sequestering agents, dyes, colorants, or any other ingredient typically used in cosmetics or dermatology.

The compositions according to the invention are formulated according to techniques which are well known to this art.

The compositions according to the invention may be in the form of a solution, a suspension, or a dispersion in solvents or fatty substances, in the form of a vesicle dispersion or, alternatively, in the form of an emulsion such as a cream or a milk, and in the form of an ointment, a gel, a solid stick, an aerosol foam or a spray.

In order to further illustrate the present invention and the advantages thereof, the following specific examples are given, it being understood that same are intended only as illustrative and in nowise limitative.

In said examples to follow, as in the foregoing description, all parts and percentages are given by weight, unless otherwise indicated.

EXAMPLE 1

The following tests demonstrated the antimicrobial activity of the combination according to the invention, this being compared with the antimicrobial activity of a lipoamino acid: N-n-octanoylglycine, marketed by Seppic under the trademark Lipacid® C8G.

Procedure

Strains used:

*Staphylococcus aureus* (ATCC 6538),

*Escherichia coli* (ATCC 8739),

*Pseudomonas aeruginosa* (ATCC 9027),

*Enterococcus faecalis* (ATCC 11700),

*Candida albicans* (ATCC 10231).

Dilutions of the test product were made in tubes in tryptone-salt broth at a proportion of 10 ml per tube.

The inoculum was a 24-hour culture of the test microorganism in the tryptone-salt nutrient broth diluted such as to provide a suspension containing from $10^5$ to $10^6$ microorganisms/ml. The inoculum was added in equal volume (10 ml) to the various dilutions of the product as well as to a control tube containing 10 ml of tryptone-salt broth.

A count was immediately taken from the broth in this control tube by seeding decimal dilutions of this broth on agar medium.

All of the tubes were incubated in aerobic atmosphere at 37° C. for 24 hours.

Reading: The CMI was the minimum concentration of product for which a culture was no longer visible. A count of the surviving microorganisms was taken by replating on agar medium of the broths in the tubes remaining without a visible culture.

The CMI results are reported in the following Tables:

Table 1: CMI of Lipacid® C8G

Table 2: CMI of the combination Lipacid® C8G/Sensiva® SC 50

+: no antimicrobial activity detected

−: antimicrobial activity detected

TABLE 1

| Concentration in % | E. coli | Pseudo. aeruginosa | Staph. aureus | Enter. faecalis | Candida albicans |
|---|---|---|---|---|---|
| 3 | − | − | − | − | − |
| 2 | − | − | − | − | − |
| 1 | − | − | − | − | − |
| 0.5 | − | − | − | − | − |
| 0.25 | − | − | − | − | − |
| 0.2 | − | − | − | − | − |
| 0.15 | − | − | − | − | − |
| 0.1 | − | − | + | − | + |
| 0.05 | + | + | + | + | + |
| 0.01 | + | + | + | + | + |

TABLE 2

| Concentration in % Lip./Sens | E. coli | Pseudo. aeruginosa | Staph. aureus | Enter. faecalis | Candida albicans |
|---|---|---|---|---|---|
| 0.5/0.5 | – | – | – | – | – |
| 0.1/0.1 | – | – | – | – | – |
| 0.1/0.05 | – | – | – | – | + |
| 0.05/0.1 | – | – | – | – | – |
| 0.05/0.05 | – | – | – | + | + |

Sensiva® SC 50, marketed by Phacogene laboratories, is the compound: 1-(2-ethylhexyl) glyceryl ether. It is known not to have any intrinsic antimicrobial activity.

Thus, entirely surprisingly, this compound lacking in antimicrobial activity exhibited a synergistic effect on the antimicrobial activity of Lipacid® C8G.

EXAMPLE 2

In this example, a composition useful as a care cream for the skin and which was in the form of an oil-in-water emulsion was formulated.

The following mixtures were prepared.

| Mixture A: | |
|---|---|
| Isocetyl stearate | 9.0% |
| Squalane | 7.0% |
| Glyceryl monostearate/polyethylene glycol stearate mixture (Arlacel ® 165 marketed by ICI) | 4.0% |
| Cetyl alcohol | 3.0% |
| Corn starch esterified with octenylsuccinic anhydride, aluminum salt (Dry-Flo Plus ®-28-1160 marketed by National Starch) | 2.0% |
| Karite butter | 2.0% |
| 1-(2-Ethylhexyl) glyceryl ether (Sensiva ® SC50) | 0.5 |
| Mixture B: | |
| Water | qs 100% |
| N-n-Octanoylglycine (Lipacid ® C8G) | 0.5% |
| Glycerol | 6.0% |
| Mixture C: | |
| Mixture of (13/87) α,ω-dihydroxy polydimethylsiloxane/ cyclotetra- and cyclopentadimethylsiloxane (56% and 44%) | 3.0% |
| Cyclomethicone | 7.0% |

Mixture A was heated to 70° C. with stirring. Mixture B was heated to 70° C. with stirring. Mixture B was transferred rapidly and under vacuum into mixture A and the resulting mixture was then emulsified for 5 minutes. It was cooled to 45° C. and mixture C was added with stirring. The entire mixture was cooled to 25° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. Combinatory antimicrobial immixture active against gram-negative bacteria comprising at least one antimicrobial hydrolipid and/or lipid and an antimicrobially synergistically effective amount of at least one glyceryl monoalkyl ether.

2. The combinatory antimicrobial immixture as defined by claim 1, comprising at least one antimicrobial hydrolipid.

3. The combinatory antimicrobial immixture as defined by claim 2, comprising at least one lipoamino acid.

4. The combinatory antimicrobial immixture as defined by claim 2, said at least one antimicrobial hydrolipid comprising a fatty acid having from 6 to 18 carbon atoms.

5. The combinatory antimicrobial immixture as defined by claim 4, said at least one antimicrobial hydrolipid comprising a fatty acid having from 6 to 12 carbon atoms.

6. The combinatory antimicrobial immixture as defined by claim 2, said at least one antimicrobial hydrolipid comprising an amino acid monomer, peptide or protein.

7. The combinatory antimicrobial immixture as defined by claim 6, said at least one antimicrobial hydrolipid comprising glycine or cysteine.

8. The combinatory antimicrobial immixture as defined by claim 1, comprising at least one lipid fatty acid having from 6 to 18 carbon atoms.

9. The combinatory antimicrobial immixture as defined by claim 1, said at least one glyceryl monoalkyl ether having the structural formula (I):

$$R-O-CH_2-CHOH-CH_2OH \qquad (I)$$

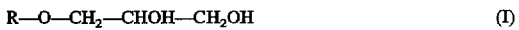

in which R is a linear or branched, saturated or unsaturated alkyl radical having from 3 to 14 carbon atoms.

10. The combinatory antimicrobial immixture as defined by claim 9, wherein formula (i), R has from 5 to 12 carbon atoms.

11. The combinatory antimicrobial immixture as defined by claim 10, wherein formula (I), R has from 7 to 12 carbon atoms.

12. The combinatory antimicrobial immixture as defined by claim 9, said at least one glyceryl monoalkyl ether comprising 1-heptyl glyceryl ether, 1-(2-ethylhexyl) glyceryl ether, 1-octyl glyceryl ether, 1-decyl glyceryl ether or 1-dodecyl glyceryl ether.

13. The combinatory antimicrobial immixture as defined by claim 1, the ratio by weight of said at least one antimicrobial hydrolipid and/or lipid to said at least one glyceryl monoalkyl ether ranging from 0.05 to 30.

14. The combinatory antimicrobial immixture as defined by claim 13, said ratio by weight ranging from 0.1 to 5.

15. A pharmaceutical/cosmetic composition comprising an antimicrobially effective amount of the combinatory immixture as defined by claim 1.

16. The pharmaceutical/cosmetic composition as defined by claim 15, adopted for topical dermatological application.

17. The pharmaceutical/cosmetic composition as defined by claim 15, comprising from 0.01% to 6% by weight of said at least one glyceryl monoalkyl ether.

18. The pharmaceutical/cosmetic composition as defined by claim 17, comprising from 0.2% to 3% by weight of said at least one glyceryl monoalkyl ether.

19. The pharmaceutical/cosmetic composition as defined by claim 17, comprising from 0.01% to 5% by weight of said at least one antimicrobial hydrolipid and/or lipid.

20. The pharmaceutical/cosmetic composition as defined by claim 19, comprising from 0.2% to 3% by weight of said at least one antimicrobial hydrolipid and/or lipid.

21. The combinatory immixture of claim 1 wherein said antimicrobial hydrolipid or lipid is N-n-Octanoylglycine and said glyceryl monoalkyl ether is 1-(2-ethylhexyl) glyceryl ether.

* * * * *